United States Patent
Berndt et al.

(10) Patent No.: US 6,599,475 B1
(45) Date of Patent: Jul. 29, 2003

(54) APPARATUS FOR PRODUCING THIN LIQUID SAMPLES FOR MICROSCOPIC ANALYSIS

(75) Inventors: Klaus W. Berndt, Timonium, MD (US); Brian G. Scrivens, Colora, MD (US); Dwight Livingston, Fallston, MD (US); Robert S. Frank, Ellicott City, MD (US)

(73) Assignee: Becton, Dickinson and Company, Franlin Lakes, NJ (US)

( * ) Notice: Subject to any disclaimer, the term of this patent is extended or adjusted under 35 U.S.C. 154(b) by 224 days.

(21) Appl. No.: 09/671,132

(22) Filed: Sep. 27, 2000

(51) Int. Cl.⁷ ................ G01N 21/00; G01N 31/22; G01N 15/06; G01N 33/00; G01N 33/48

(52) U.S. Cl. ............... 422/58; 422/50; 422/55; 422/61; 422/68.1; 422/73; 422/82.05; 422/100; 422/101; 422/102; 422/104; 436/69; 436/63; 436/66; 436/70; 436/174; 436/177; 436/180

(58) Field of Search ............ 422/99, 50, 68.1, 422/82.05, 102, 73, 100, 101, 104, 44, 72; 430/180; 436/526, 69; 356/246

(56) References Cited

U.S. PATENT DOCUMENTS

| | | | | |
|---|---|---|---|---|
| 4,963,498 A | * | 10/1990 | Hillman et al. | 438/69 |
| 5,302,348 A | * | 4/1994 | Cusack et al. | 422/73 |
| 5,472,671 A | * | 12/1995 | Nilsson et al. | 422/102 |
| 5,707,799 A | * | 1/1998 | Hansmann et al. | 435/6 |
| 5,731,212 A | * | 3/1998 | Gavin et al. | 436/526 |
| 6,002,475 A | * | 12/1999 | Boyd et al. | 356/246 |
| 6,153,148 A | * | 11/2000 | Thomas | 422/72 |
| 6,180,314 B1 | * | 1/2001 | Berndt | 430/180 |
| 6,188,474 B1 | * | 2/2001 | Dussault et al. | 356/246 |

* cited by examiner

Primary Examiner—Jill Warden
Assistant Examiner—Brian Sines
(74) Attorney, Agent, or Firm—Bruce S. Weintraub

(57) ABSTRACT

The present invention relates to the field of diagnostics by means of microscopic sample analysis, and specifically relates to a method and apparatus for preparing thin microscopic samples of liquids, and in particular monolayers of red blood cells.

20 Claims, 8 Drawing Sheets

APPARATUS FOR PRODUCING THIN LIQUID SAMPLES FOR MICROSCOPIC ANALYSIS

FIELD OF THE INVENTION

The present invention relates to the field of diagnostics by means of microscopic sample analysis, and specifically relates to a method and apparatus for preparing thin microscopic samples of liquids, and in particular monolayers of red blood cells.

BACKGROUND OF THE INVENTION

Microscopic examination of blood films is an important part of the hematologic evaluation. Today, three methods for preparing thin blood films are in use, namely the "wedge-slide method", the "spinner method" and the "coverglass method" (see, e.g. "Clinical Diagnosis and Management by Laboratory Methods", Nineteenth Edition, 1996, edited by John B. Henry).

In the "wedge-slide method", a drop of blood is placed onto a slide that is on a flat surface. A second (spreader) slide is pressed at an angle of 30 to 45 degrees against the first slide and moved along the first slide, which results in the formation of a moderately thin blood film that is then dried in air. The quality of the generated blood smear will strongly depend on the personal skill level of the technician. To overcome the need for highly skilled personnel, both manual apparatus (U.S. Pat. No. 4,494,479 to Drury) and automated apparatus (U.S. Pat. No. 4,407,843 to Sasaki; U.S. Pat. No. 3,683,850 to Grabhorn; U.S. Pat. No. 3,880,111 to Levine et al.; U.S. Pat. No. 4,392,450 to Prevo; WO 9,641,148 to Levine et al.) for executing the wedge-slide method have been proposed.

In addition to being time consuming, the physical action of the spreader slide tends to distort the morphology of many of the cells. In view of this, an alternative method for the preparation of blood samples known as the "spinner method" has been proposed (see, for example, U.S. Pat. No. 5,549,750 to Kelley) wherein a drop of blood is disposed onto a slide which is then spun to create a monolayer of randomly distributed red blood cells (RBCs). It has been found, however, that drying of the red blood cells produces undesirable types of distortions, particularly a loss of central pallor for many of the RBCs as they dry. It is not entirely clear what causes these shape changes, but they apparently are caused by surface tension, charges and/or drying effects. To inhibit cell morphology distortions from occurring during drying, it has been proposed to preserve the morphologies by applying fixing agents after forming the monolayer, but prior to drying (U.S. Pat. No. 4,209,548 to Bacus; U.S. Pat. No. 4,483,882 to Saunders).

The wedge-slide method as well as the spinner method require relatively complex apparatus and involve time consuming procedures. A simpler way to produce blood films is the "coverglass method" where two quadratic coverglasses are being used. A first glass, with a drop of blood attached to the center of the underside, is placed crosswise on a second glass so that the corners appear as an eight-pointed star. If the drop is not too large and if the glasses are perfectly clean, the blood will spread out evenly and quickly in a thin layer between the two surfaces. After spreading stops, the two glasses are pulled apart on a plane parallel to their surfaces. The two blood films are then dried in air.

While the coverglass method does not require auxiliary apparatus, the quality of the blood smears will again depend strongly on the skill level of the technician performing the procedure. Moreover, executing the method includes increased risk because the thin pieces of glass that contain the blood sample may break during the separation step. And, finally, drying the blood films may cause changes in the cell morphology.

It has been suggested, in U.S. Ser. No. 09/085,851, to produce thin liquid samples for microscopic analysis by (1) arranging spacers on a microscope slide outside of the slide's center, by (2) disposing a drop of blood onto the microscope slide near to its center, by (3) positioning a flexible coverglass onto the spacers, by (4) applying a downward force to the center of the flexible coverglass so that the coverglass touches the blood, and by (5) suspending the application of said force. In the moment the coverglass is touching the drop of blood, the blood is spreading outwards and adhesion forces hold the flexible coverglass down so that a very thin layer of liquid is formed.

While this method provides thin layers of blood, and in particular monolayers of isolated red blood cells, it is still quite labor-intensive. More specifically, the positioning of the flexible coverglass onto the spacers requires concentration from the operator. There are also concerns that the thin coverglass may break during operation, and the possibility that the operator may be injured. Moreover, the application of the downward force requires some degree of training.

For the production of monolayers of red blood cells, it has also been suggested (S. Wardlaw, "Analysis of quiescent anticoagulated whole blood samples", U.S. Ser. No. 09/249, 721 and S. Wardlaw, "Calibration of a whole blood sample analyzer", U.S. Ser. No. 09/248,135) to design a cuvette-like optical sample container for the cell suspension that has different optical pathlengths in different areas. In at least one area, the thickness of the liquid layer of un-diluted blood is so thin (2 to 7 microns) that monolayers of isolated RBCs are formed. In another region, the liquid layer is thicker (7 to 40 microns), and typical chain-like aggregates of RBCs ("Roleaux") are forming. The thick area is used to determine the hematocrit (HCT), and the thin area is used to determine the volume of single red blood cells (RCV). As has been found by the inventors of the present invention, the formation of a monolayer of red blood cells in a cuvette having areas of different thickness according to prior art is often impaired and may not be reliable.

The use of compartments of different thickness in the prior art is necessary for allowing the determination of the RCV and the HCT. The HCT can not be measured within the monolayer region, and the RCV can not be determined within the Roleaux region. RCV and HCT are usually determined employing the principle of fluorescence volume exclusion. In this method, the plasma is stained with a fluorescent dye, and the RCV as well as the HCT are measured by determining the partial volume that is excluded from emitting fluorescence by the RBCs. The principle relies on homogeneous excitation intensity throughout the whole sample volume, and also on homogeneous photon collection efficiency throughout the whole sample volume. FIG. 1 shows a plot of the excitation intensity along the z-axis within a microscope, assuming an objective lens with a numerical aperture, NA=0.4, and an excitation center-wavelength of 500 nm. A similar situation applies to the photon collection efficiency through the objective lens. Due to the lack of homogeneous excitation and homogeneous photon collection, the determination of the HCT in a cuvette of thickness between 15 and 40 $\mu$m is somewhat problematic.

In view of the above problems there is a need for a reliable way to produce monolayers of isolated RBCs. There is also a need for a method for determining the HCT of whole blood in a cuvette having a height below 10 μm.

SUMMARY OF THE INVENTION

It is an objective of the present invention to provide a method and apparatus to produce thin samples of liquids for microscopic analysis, and in particular thin samples of whole blood, whereby monolayers of isolated red blood cells are formed, and whereby the undiluted sample's HCT can be determined from a measurement within the monolayer.

According to the present invention, the above objective is achieved with an optical cuvette with at least one transparent window, whereby said cuvette has a thickness below a certain value, whereby the interior of the cuvette is separated into a plurality of successive compartments by means of separating walls, whereby each separating wall comprises a first type of through-channel allowing RBCs and blood plasma to flow through, and whereby each separating wall comprises also a second type of through-channel allowing only blood plasma to flow through, the channels being designed in a way that a significant percentage of the RBCs arriving at a separating wall can pass through, so that the particle dilution per separating wall is relatively low, whereby the liquid sample enters the first of the compartments through an entrance, where there are small venting openings in the compartments to allow for air venting during filling, and whereby characteristic parameters of the blood sample entering the cuvette are determined by analyzing the monolayer of isolated RBCs that forms within the last compartment, using the principles of fluorescence volume exclusion and/or absorption volume exclusion in connection with a microscope.

According to the present invention, the thickness of the cuvette should be so small that no Roleaux formation develops within the one compartment that is farthest away from the entrance. A typical device according to the present invention has a height preferably between 3 and 10 μm, comprises preferably at least five separating walls, whereby each of the separating walls allows one half of the arriving RBCs to pass through. This results in an overall "dilution" allowing for the formation of monolayers of isolated RBCs in the compartment farthest away from the entrance. The HCT value of the sample entering the cuvette can be determined from a measurement of the HCT value within the last compartment.

BRIEF DESCRIPTION OF THE DRAWINGS

FIG. 7(a) represents a view from the top to the bottom of the separating wall. FIG. 7(b) represents a side-view of the separating wall.

FIG. 8(a) represents a view from the top to the bottom of the separating wall. FIG. 8(b) is a side-view of the separating wall, looking in flow direction. FIG. 8(c) is a side-view of the separating wall, looking against the flow direction. FIG. 8(d) shows a cross-section through the separating wall within a section comprising a through-channel of the second type.

DETAILED DESCRIPTION OF THE PRESENT INVENTION

It is an objective of the present invention to provide a method and apparatus to produce thin samples of liquids for microscopic analysis, and in particular thin samples of whole blood, whereby monolayers of isolated RBCs are formed, and whereby the undiluted sample's HCT can be determined from a measurement within the monolayer.

According to the present invention, this objective is achieved with an optical plan-parallel cuvette with at least one transparent window, whereby said cuvette has a thickness small enough to prevent the development of typical Roleaux formations. A typical optical cuvette according to the present invention has a thickness preferably between 3 and 10 μm. The interior of the cuvette is separated into a plurality of successive compartments by means of separating walls, whereby each separating wall comprises a first type of through-channel allowing RBCs and blood plasma to flow through, and whereby each separating wall comprises also a second type of through-channel allowing only blood plasma to flow through. The channels are designed in a way that a significant percentage of the RBCs arriving at a separating wall can pass through, so that the particle dilution per separating wall is relatively low. The liquid sample enters the first of the compartments through an entrance, which may be a narrow channel coming from a sample entry port. The walls in each of the compartments of the cuvette are equipped with small venting openings for air venting during filling.

Figure 2:
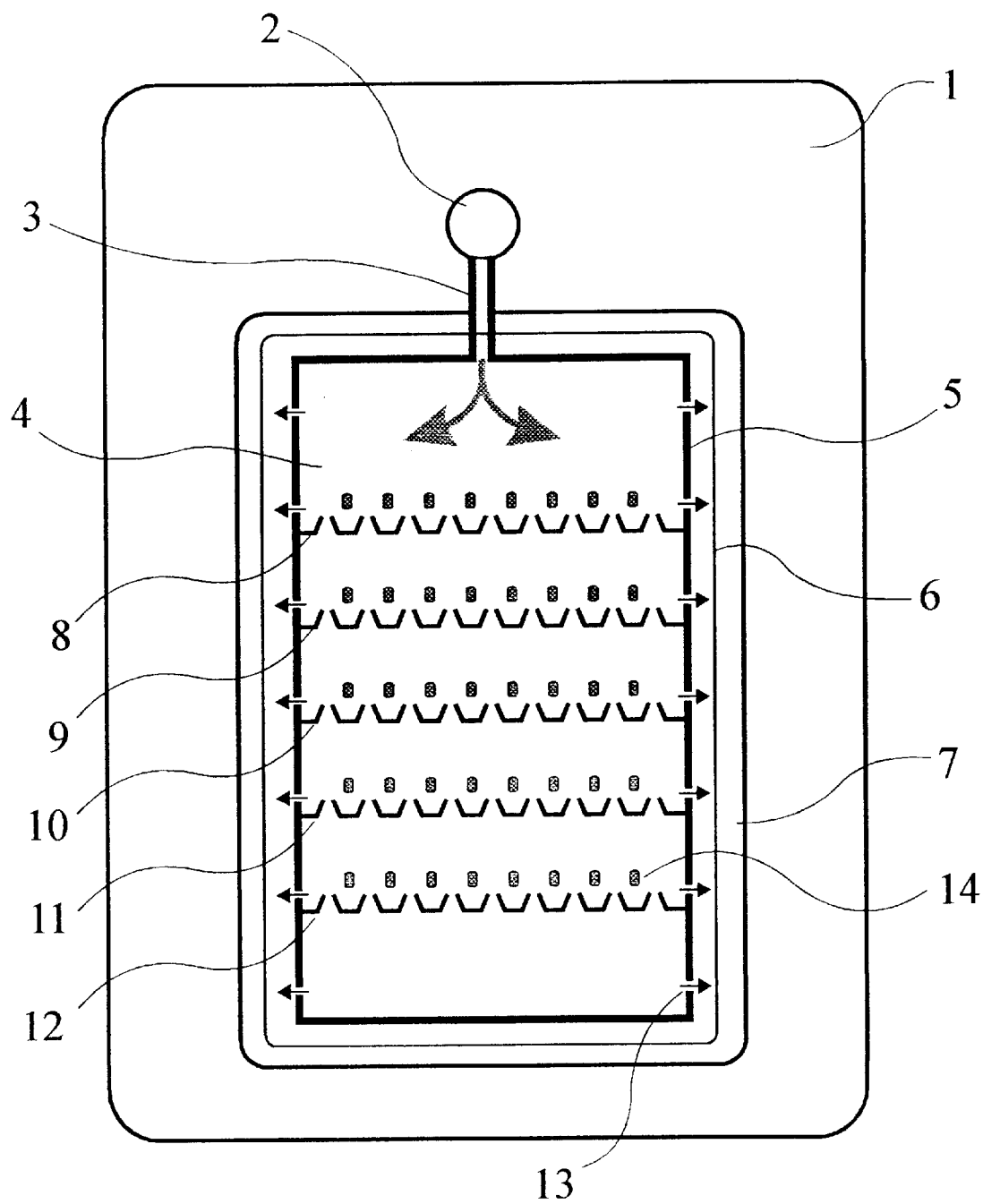
FIG. 2 depicts schematically an optical cuvette according to the present invention.

FIG. 2 shows schematically a preferred embodiment of an optical cuvette according to the present invention. The cuvette is arranged on a base plate (1), typically made out of a plastic material such as polycarbonate or polystyrene. Base plate (1) has a sample entry port (2) that is connected with the interior of a cuvette (4) via a narrow channel (3). Channel (3) has a higher capillarity than entry port (2), and cuvette (4) is so thin that it has a higher capillarity then channel (3). Therefore a sample liquid such as fluorescently stained whole blood will flow from entry port (2) through channel (3) into cuvette (4). Cuvette (4) is divided into a multitude of compartments. In the example of a cuvette as shown in FIG. 2, cuvette (4) is divided into six compartments by five separating walls (8, 9, 10, 11, and 12). Cuvette (4) has a transparent lid (6) that acts as an optical window to allow for fluorescence measurements under a microscope in EPI configuration. Since base plate (1) can be made out of a transparent plastic material, cuvette (4) can have also two windows, which would allow performing transmission measurements.

Lid (6) is resting on walls (5) that carry venting holes (13) in each of the compartments to allow for air escape during filling. Walls (5) determine the thickness of the optical cuvette (4). To guarantee a constant thickness across the whole cuvette, separating walls (8 to 12) are equipped with weld features (14). Good stability is achieved when lid (6) is welded ultrasonically onto walls (5) and weld features (14), but other methods can be used also. Walls (5) of cuvette (4) are surrounded by a moat (7), making sure that lid (6) is resting only on walls (5) and weld features (14). Moat (7) also provides the necessary space outside of cuvette (4) to allow for free air escape through openings (13) during filling. Separating walls (8 to 12) can have many different designs, and particular examples are described below. However, according to the present invention, separating walls (8 to 12) have to be designed so that a significant percentage of the RBCs approaching each wall have a chance to pass through. This is a fundamental difference to proposals of the prior art, where the necessary "RBC dilution" has been attempted in one step. In allowing a significant percentage of the arriving RBCs to pass through the separating walls, partial clogging in front of the separating walls will not occur, and the dilution efficiency becomes predictable. Consequently, the overall dilution becomes predictable, and parameters of the sample entering the cuvette can be determined from measurements within the diluted sample.

Figure 3:
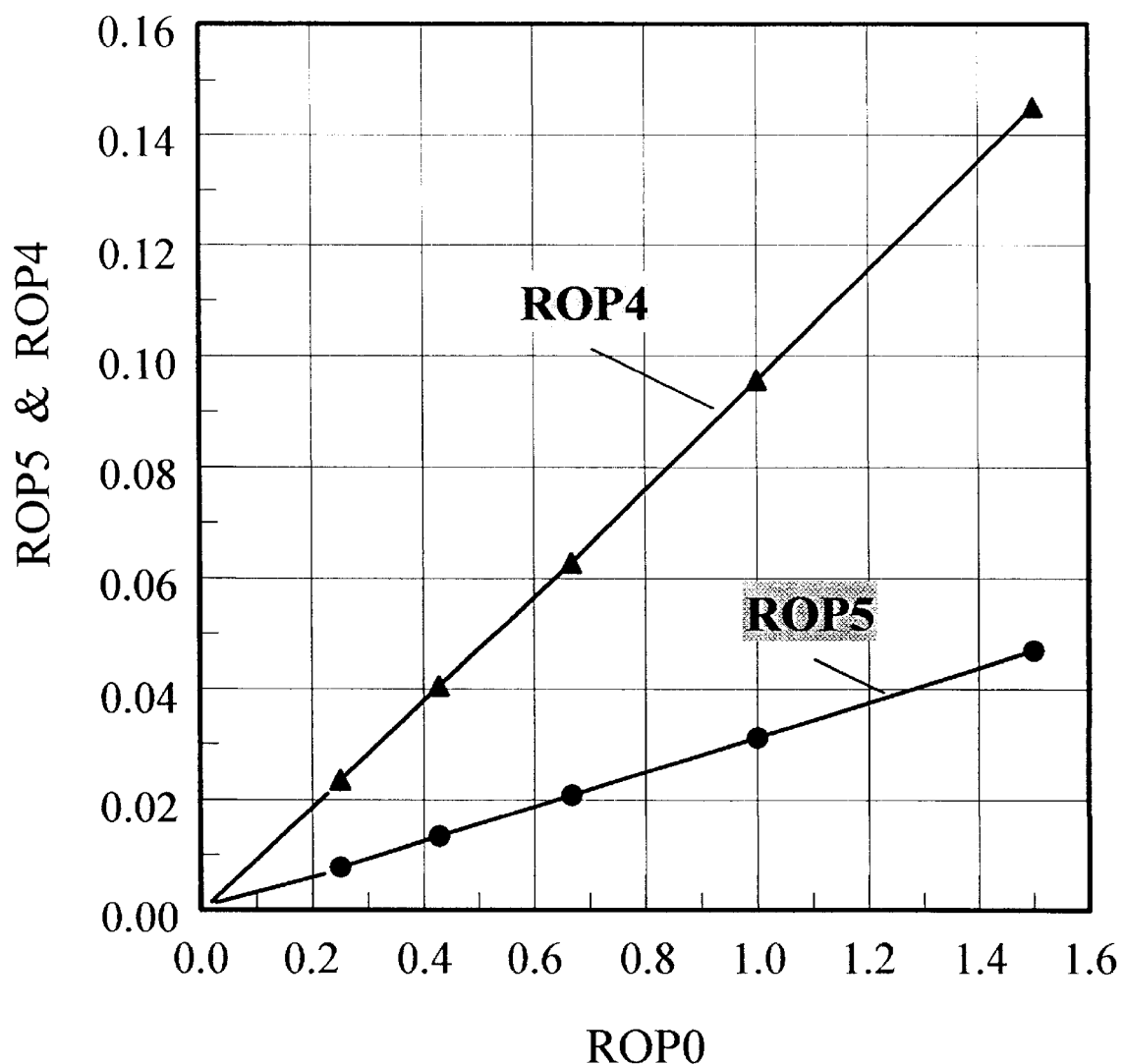
FIG. 3 shows the ratio "red-cell-volume-over-plasma-volume", or ROP, after the fourth and fifth separating wall within a cuvette according to the present invention as a function of the starting value, ROP0, for the sample entering the device.

A particular example is discussed below in more detail. It is assumed that each of the separating walls allows one half of the arriving RBCs to pass through, and that the influx of sample liquid comes to a stop after all compartments have been filled. FIG. 3 shows the ratio "red-cell-volume-over-plasma-volume", ROP, after the fourth (=ROP4) and fifth (=ROP5) separating wall as a function of the starting value, ROP0, for the sample entering the device. The ratio ROP is related to HCT via the equation $$ROP = \frac{HCT}{1-HCT} * 100\% \quad (1)$$

The relation between ROP and HCT is shown for typical values in the following table:

TABLE 1

Relation between ROP and HCT

| HCT (%) | 20 | 30 | 40 | 50 | 60 |
|---|---|---|---|---|---|
| ROP | 0.2500 | 0.4286 | 0.6666 | 1.0000 | 1.5000 |

From FIG. 3 it can be observed that the quantities ROP4 and ROP5 depend linearly on the starting value ROP0. This linear relationship does not exist for HCT and the number of RBCs, an aspect that is discussed below. The straight lines in FIG. 3 can be described by $$ROP5 = 0.03128 * ROP0 \quad (2)$$

and $$ROP4 = 0.09727 * ROP0 \quad (3)$$

According to the present invention, the values of ROP5 or ROP4 that are measured after the fifth or after the fourth separating wall can be used to calculate the corresponding value ROP0 for the whole blood sample entering the optical cuvette at the first compartment. By combining equation (3) or (2) with equation (1), the HCT of the sample entering the cuvette can be calculated.

Figure 4:
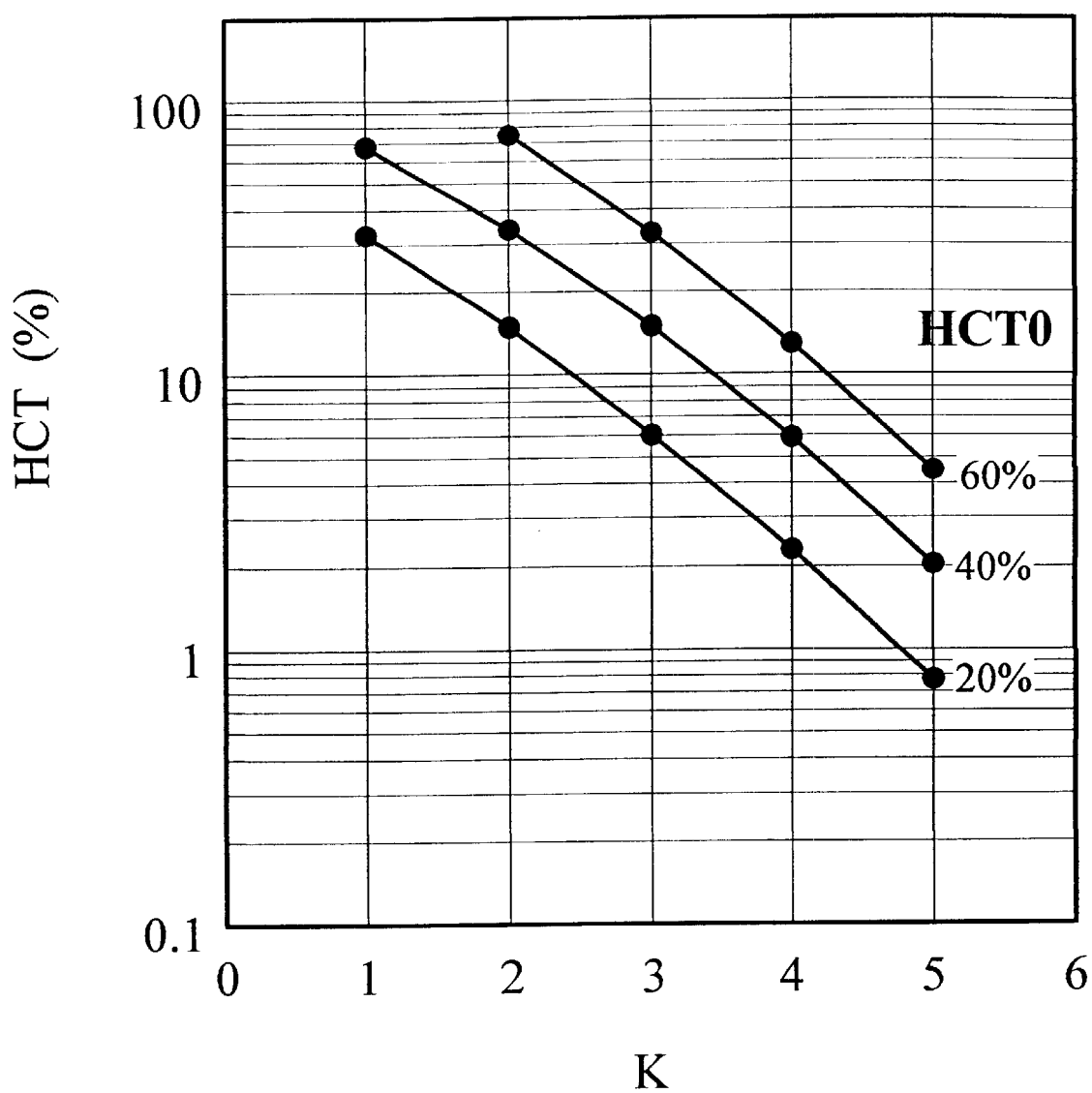
FIG. 4 shows the HCT value after each separating wall within a cuvette according to the present invention, assuming three different starting values, HCT0, for the sample entering the device.

FIG. 4 shows the HCT value after each separating wall within a cuvette according to the present invention, assuming three different starting values, HCT0 equal to 20%, 40% and 60%, for the sample entering the device at the first compartment. FIG. 4 shows that also measurements behind the third or second separating wall would allow one to calculate blood parameters of the undiluted sample entering the cuvette in the first compartment. However, since behind the fifth (and maybe behind the fourth) separating wall there will form monolayers of isolated RBCs, measurements behind those separating walls would be much easier and more reliable.

Figure 5:
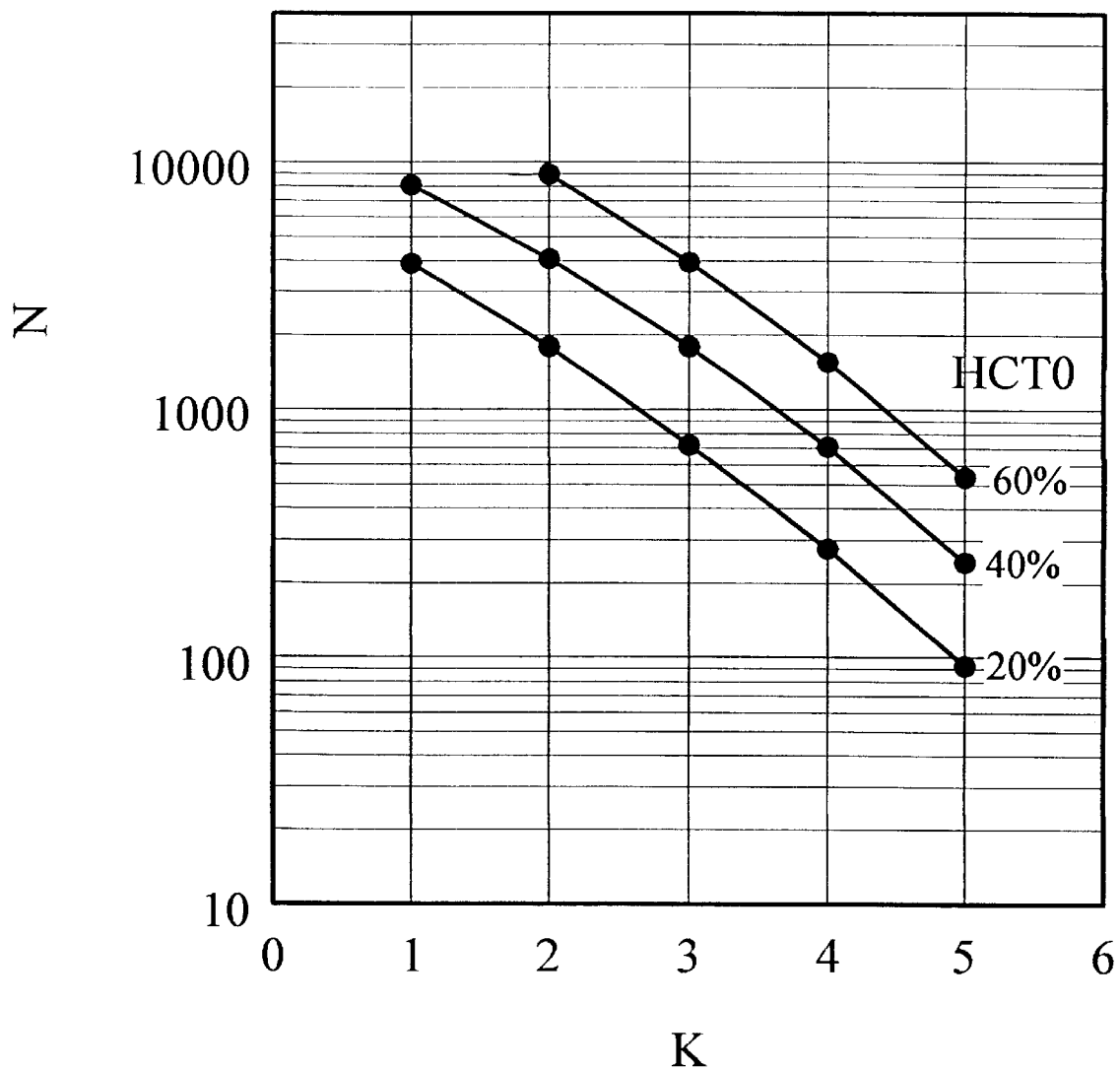
FIG. 5 shows the number of RBCs, N, within a field of size 600 μm×600 μm×3 μm after each separating wall within a cuvette according to the present invention, assuming three different starting values, HCT0, for the sample entering the device.

FIG. 5 shows the number of RBCs, N, within a field of size 600 $\mu$m ×600 $\mu$m×3 $\mu$m after each separating wall within a cuvette according to the present invention, assuming three different starting values, HCT0, for the sample entering the device. From this figure we see that behind the fifth separating wall there can be expected between 100 and 600 RBCs, a number big enough to allow for good statistics.

Figure 6:
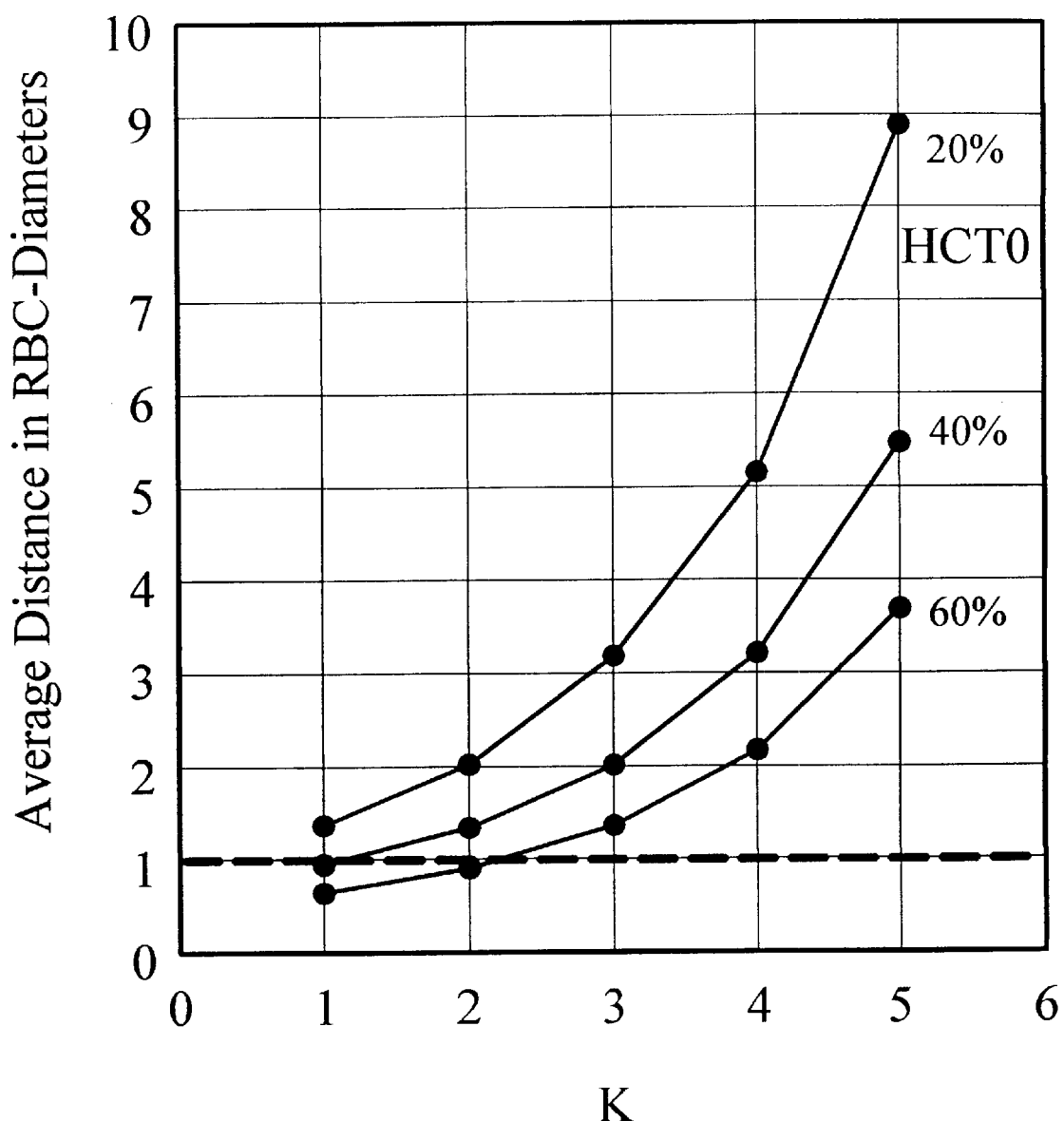
FIG. 6 shows the average distance in RBC-diameters (~7 μm) between neighboring RBCs within a field of size 600 μm×600 μm×3 μm after each separating wall within a cuvette according to the present invention, assuming three different starting values, HCT0, for the sample entering the device.

FIG. 6 shows the same data as FIG. 5, but expressed as the average distance between neighboring RBCs, measured in RBC-diameters (~7 $\mu$m) within a field of size 600 $\mu$m×600 $\mu$m×3 $\mu$m. After the fifth separating wall, the average distance between neighboring RBCs for clinically relevant HCT values is between three and nine RBC diameters. Consequently, there are optimum conditions for the formation of a monolayer of isolated RBCs behind the fifth separation wall.

A cuvette according to the present invention is suitable for microscopic analysis of whole blood samples using the principle of fluorescence volume exclusion or absorption volume exclusion. The cuvette can be placed on the sample stage of a common fluorescence microscope in EPI configuration, or onto the sample stage of a common transmission microscope.

Figure 1:
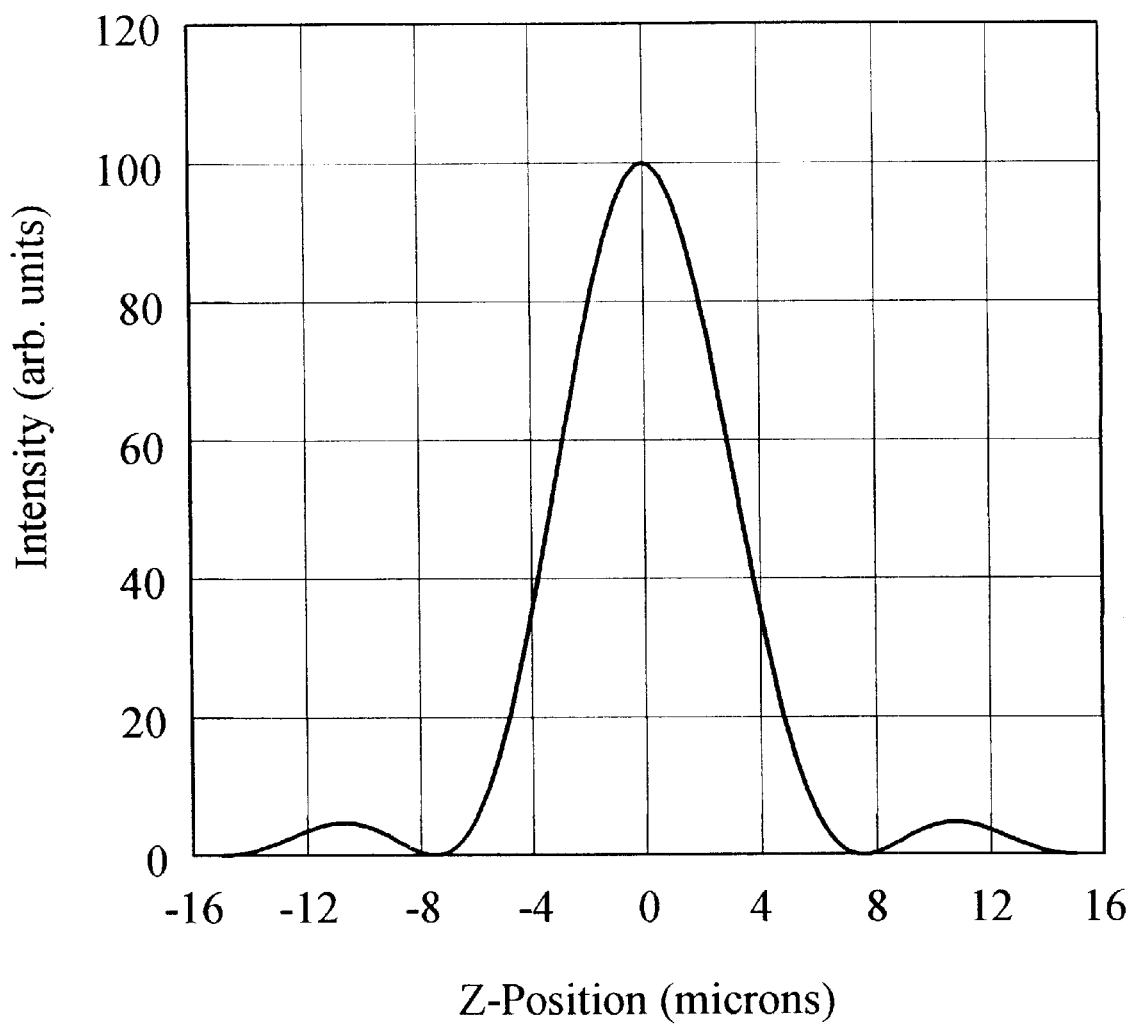
FIG. 1 illustrates the excitation intensity along the Z-axis below a typical microscope objective lens having a numerical aperture NA=0.4 for an excitation center wavelength of 500 nm. A similar curve exists describing the photon collection efficiency. In a microscope in EPI configuration, the convolution of both curves applies.

Due to the fact that the cuvette has a relatively small thickness, e.g. 3 $\mu$m, a substantially even illumination and photon collection can be achieved (see FIG. 1), in contrast to prior art cuvettes that involve a varying thickness, and in particular thickness values up to 40 $\mu$m. An additional advantage can be seen in the fact that perfect imaging can be achieved with only one single adjustment of the cuvette's Z-position.

As has been mentioned above, a variety of designs for the separation walls is possible. The important point is that a substantial percentage (e.g. one half) of the arriving RBCs must have a chance to pass through. In this way, partial clogging is prevented from happening, and a reliable generation of monolayers of isolated RBCs can be achieved. In practice, it is advisable to determine the parameters in equation (2) or (3) via a one-time calibration for a particular separation wall design. In other words, one would measure ROP values behind the fifth or fourth separation wall, and would compare them with the corresponding parameters of the undiluted sample by employing an independent reference method.

Figure 7:
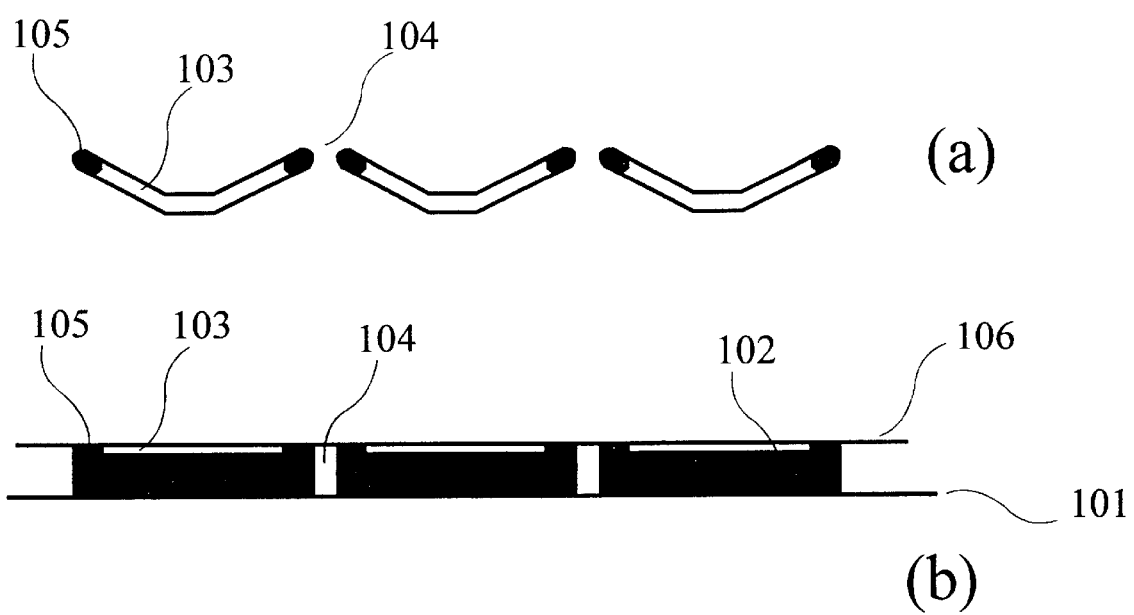
FIG. 7 shows an example of a separating wall comprising different types of through channels.

FIG. 7 illustrates an example of a separating wall in an optical cuvette according to FIG. 2. Welding features (14) in FIG. 2 are not considered as part of the separation wall, and are, therefore, not shown. While FIG. 7a represents a view from the top (106) to the bottom (101), FIG. 7b shows a side-view of the separating wall.

In FIGS. 7a and 7b, (101) represents the upper surface of base plate (1) as shown in FIG. 2, and (106) represents the lower surface of lid (6) as shown in FIG. 2. To provide stability and precision to the optical cuvette, lid (6) is resting on separation wall (102) at profile features (105). A first type of through-channel (104) allows RBCs and blood plasma to flow through. A second type of through-channels (103) allows only blood plasma to flow through.

In the example given in FIG. 7, the percentage of the arriving RBCs that will pass through the separation wall is dependent on the relative sizing of through-channels (104) and (103).

Figure 8:
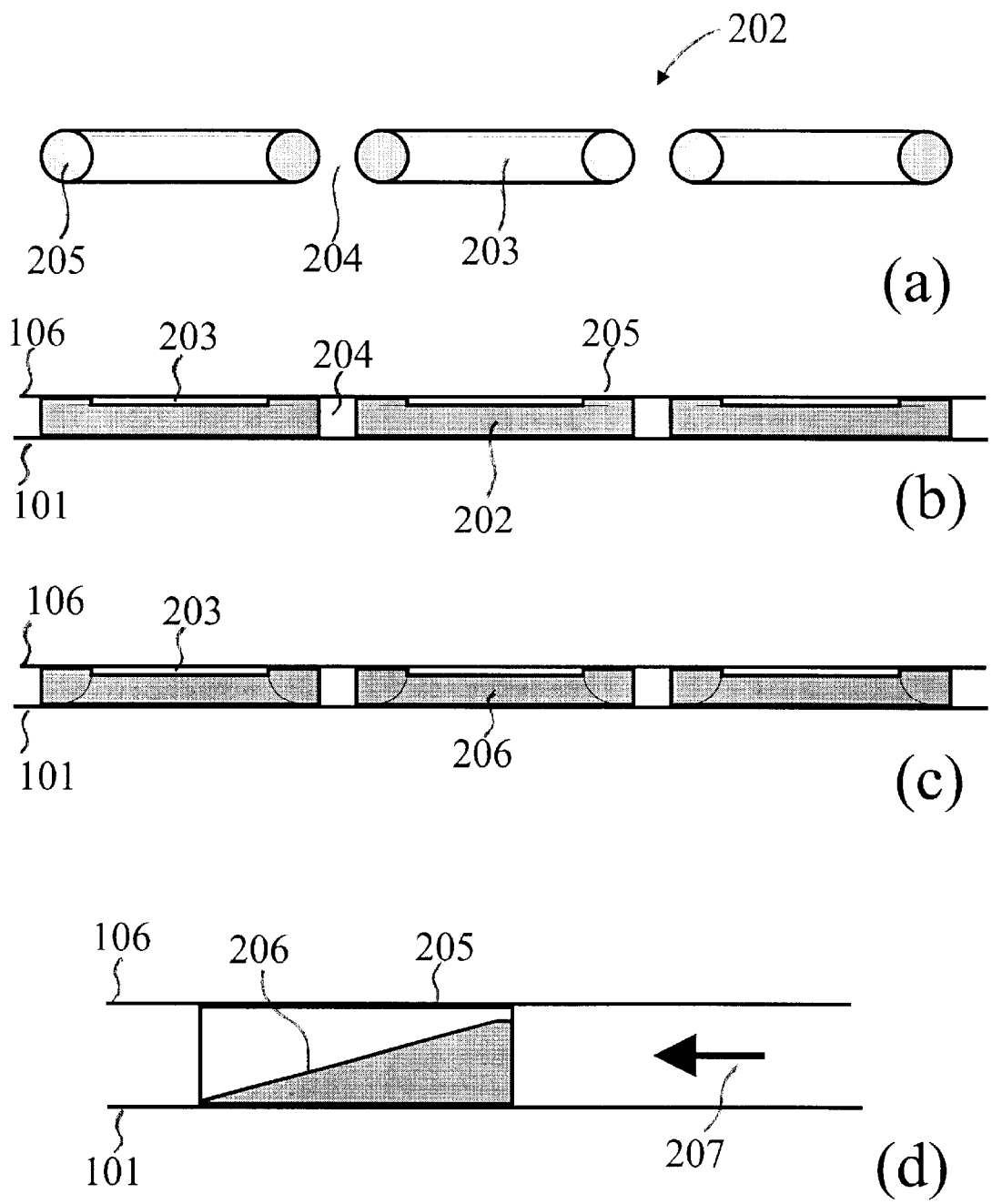
FIG. 8 shows a second example of a separating wall comprising different types of through channels.

FIG. 8 shows a second example of a separating wall comprising different types of through-channels.

FIG. 8 shows part of a separation wall (202), where (101) represents the upper surface of base plate (1) as shown in FIG. 2, and (106) represents the lower surface of lid (6) as shown in FIG. 2. Lid (6) of FIG. 2 is resting on separation wall (202) at profile features (205). Again, a first type of through-channels (204) allows RBCs and blood plasma to flow through, and a second type of through-channels (203) allows only blood plasma to flow through.

FIG. 8 (a) represents a view from the top (106) to the bottom (101). FIG. 8 (b) is a side-view of separating wall (202), looking in flow direction. FIG. 8 (c) is a side-view of separating wall (202), looking against the flow direction. FIG. 8 (d) shows a cross-section through separating wall (202) within a section comprising a through-channel of the second type (203). As can be seen from FIGS. 8 (c) and (d), through-channels (203) have an asymmetric profile in flow direction like a water dike. At the entrance (208) of channel (203), the channel is narrow, which results in a high papillarity. Consequently, the blood plasma is drawn into the channel. At the exit (209) of through-channel (203), the channel is as wide as the compartment itself, and any sharp corners are avoided. As a consequence, there is no jump in capillarity, and the blood plasma continues to flow into the adjoining compartment.

By sizing the two types of through-channels, any desired passing percentage for the arriving RBCs can be obtained. Microfluidic systems, and in particular small channels of micrometer dimensions, typically have a tendency towards laminar flow patterns. An optical cuvette according to the present invention has micrometer dimensions in only one direction, while the two other directions are more macroscopic. However, in spite of this, it is advantageous to arrange consecutive separation walls within the chamber with a certain longitudinal relative shift to each other. One option would be to shift each consecutive separation wall longitudinally by one half "pitch". In doing so, possible "through-shooting" of red blood cells will be prevented.

What is claimed is:

1. An apparatus for producing thin samples of liquids for microscopic analysis, said apparatus comprising:
   a base portion;
   a means for containing said sample(s) carried by said base portion, having an interior, an exterior, and outside walls; and
   a lid portion,
   the base portion, said means and the lid forming a cuvette,
   wherein said cuvette has a plurality of consecutive separation walls which separate the interior of said cuvette into a plurality of successive compartments;
   wherein said cuvette has a sample entrance port that is connected with the first of said successive compartments by a channel,
   wherein each of said consecutive separation walls comprises at least two different types of through-channels, and
   wherein the liquid sample is analyzed within the last of said successive compartments.

2. The apparatus according to claim 1 wherein said liquid is blood.

3. The apparatus according to claim 1 wherein said base portion is a base plate.

4. The apparatus according to claim 2 wherein said cuvette has a thickness small enough so that for a sample of undiluted whole blood entering said entrance port, and passing through all of said through-channels in said consecutive separation walls between said successive compartments, the average distance between neighboring red blood cells in the last of the successive compartments is greater than the typical red blood cell diameter.

5. The apparatus according to claim 1 wherein said cuvette has a thickness of between about 3 and 10 $\mu$m.

6. The apparatus according to claim 2, wherein each separating wall of said cuvette comprises:
   a) at least one through-channel of a first type which allows red blood cells and blood plasma to flow through said wall; and
   b) at least one through-channel of a second type which allows only blood plasma to flow through said wall.

7. The apparatus according to claim 1 wherein each wall of each compartment of said cuvette has at least one small venting opening for air venting.

8. The apparatus according to claim 2 wherein each wall of each compartment of said cuvette has at least one small venting opening for air venting.

9. The apparatus according to claim 1 wherein said base plate is comprised of polycarbonate or polystyrene.

10. The apparatus according to claim 1 wherein said sample entrance is a sample entry port in the base portion which is connected to the means by a narrow channel.

11. The apparatus according to claim 1 wherein said separating walls of said means have weld features.

12. The apparatus according to claim 11 wherein said outside walls of said means are surrounded by a moat, so that the lid portion rests only on the outside walls and weld features.

13. The apparatus according to claim 1 wherein said lid portion is a transparent lid.

14. The apparatus according to claim 13 wherein said transparent lid is made out of plastic material.

15. The apparatus according to claim 11 wherein said lid portion is welded onto the outside walls and weld features of said means.

16. The apparatus according to claim 13 wherein said base plate is comprised of a transparent plastic material, providing said cuvette with two windows for performance of transmission measurements.

17. The apparatus of claim 2 wherein said separation walls are arranged in consecutive longitudinal fashion.

18. The apparatus of claim 1 wherein said sample container has at least five separating walls.

19. The apparatus of claim 2 wherein said cuvette has at least one window for performance of fluorescence measurements.

20. The apparatus of claim 2 wherein said cuvette has at least two windows for performance of transmission measurements.

* * * * *